United States Patent [19]
Illig et al.

[11] Patent Number: 5,340,564
[45] Date of Patent: Aug. 23, 1994

[54] FORMULATIONS COMPRISING OLIN 10-G TO PREVENT PARTICLE AGGREGATION AND INCREASE STABILITY

[75] Inventors: Kathleen J. Illig, Phoenixville; Pramod Sarpotdar, Malvern, both of Pa.

[73] Assignee: Sterling Winthrop Inc., New York, N.Y.

[21] Appl. No.: 988,564

[22] Filed: Dec. 10, 1992

[51] Int. Cl.$^5$ .............. A61K 9/14; A61K 31/075
[52] U.S. Cl. .......................................... 424/9; 424/5; 424/489; 424/499; 514/5; 514/718; 514/975
[58] Field of Search ............ 424/5, 9, 489, 499; 514/5, 718, 975

[56] References Cited

U.S. PATENT DOCUMENTS

| | | | |
|---|---|---|---|
| 4,406,878 | 9/1983 | DeBoer | 424/5 |
| 4,540,602 | 9/1985 | Motoyam et al. | 427/213.31 |
| 4,680,171 | 7/1987 | Shell | 424/5 |
| 4,680,259 | 7/1987 | Combo et al. | 435/11 |
| 4,744,989 | 5/1988 | Payne et al. | 424/490 |
| 5,019,370 | 5/1991 | Jay et al. | 424/4 |
| 5,114,703 | 5/1992 | Wolf et al. | 424/5 |
| 5,135,844 | 8/1992 | Bagchi et al. | 430/546 |
| 5,141,739 | 8/1992 | Jung et al. | 424/4 |
| 5,145,684 | 9/1992 | Liversidge et al. | 424/489 |
| 5,186,922 | 2/1993 | Shell et al. | 128/654 |

FOREIGN PATENT DOCUMENTS

498482A2  8/1992  European Pat. Off. .

Primary Examiner—Gary E. Hollinden
Attorney, Agent, or Firm—William J. Davis

[57] ABSTRACT

This invention discloses a composition comprised of nanoparticles having p-isononylphenoxypoly (glycidol) as a surface modifier adsorbed on the surface thereof. In preferred embodiments, the p-isononylphenoxypoly (glycidol) provides resistance to particle aggregation during heat sterilization. In another preferred embodiment, those nanoparticles also comprise a stability enhancing compound. A preferred stability enhancing compound is albumin. This invention further discloses a method of making nanoparticles having p-isononylphenoxypoly(glycidol) as a surface modifier adsorbed on the surface, comprised of contacting said nanoparticles with p-isononylphenoxypoly(glycidol) for a time and under conditions sufficient to form a p-isononylphenoxypoly(glycidol) surface modified nanoparticle. In a preferred embodiment, the p-isononylphenoxypoly (glycidol) surface modified nanoparticle is further contacted with a stability enhancing compound for a time and under conditions sufficient to form a p-isononylphenoxypoly(glycidol) surface modified nanoparticle with a stability enhancing compound associated therewith.

8 Claims, 4 Drawing Sheets

FORMULATIONS COMPRISING OLIN 10-G TO PREVENT PARTICLE AGGREGATION AND INCREASE STABILITY

FIELD OF THE INVENTION

This invention relates to therapeutic and diagnostic compositions with a surfactant, and to a method for the preparation thereof.

BACKGROUND OF THE INVENTION

Nanoparticles, described in U.S. Pat. No. 5,145,684, are particles consisting of a poorly soluble therapeutic or diagnostic agent onto which are adsorbed a non-crosslinked surface modifier, and which have an average particle size of less than about 400 nanometers (nm).

Sterilization of therapeutic and diagnostic agents in nanocrystalline form stabilized by a surface modifier (surfactant) is difficult. Filtration using a filter of 0.22 $\mu$m mesh size is sufficient to remove most bacteria and viruses, but the nanoparticles, due to their sizes, cannot be sterile filtered without accounting for substantial drug losses. Conventional autoclaving (steam heat) at 121° C. generally results in substantial growth in particle size, rendering the resulting particles unusable. One possible explanation is that the aggregation of nanoparticles upon heating is related to the precipitation of the surface modifier (surfactant) at or below sterilization temperature (above the cloud point of the surfactant) where the bound surfactant molecules are likely to dissociate from the nanoparticles and precipitate, leaving the nanoparticles unprotected. The unprotected nanoparticles can then aggregate into clusters of particles. Upon cooling, the surfactant redissolves into the solution, which then coats the aggregated particles and prevents them from dissociating into smaller ones.

Shelf stability of nanoparticles is also a problem, with nanoparticle size increasing upon storage. It would be advantageous to allow for an increase in storage shelf life after autoclaving without the concomitant agglomeration of the nanoparticle suspension. It is desirable that the nanoparticles exhibit good physical stability, i.e., shelf stability and stability in biological fluids, both before and after autoclaving.

This invention is directed to novel compositions that allow autoclaving of nanoparticles with reduced or no particle size growth. These compositions provide for a surfactant adsorbed onto nanoparticles such that the nanoparticles do not agglomerate during autoclaving. This invention is also directed to a method of making such compositions.

This invention is also directed to novel compositions that allow autoclaving of nanoparticles without the concomitant increase in particle size upon storage, and a method of making such compositions.

BRIEF SUMMARY OF THE INVENTION

This invention is directed to a composition comprised of nanoparticles having p-isononylphenoxypoly(glycidol) as a surface modifier adsorbed on the surface thereof. In a preferred embodiment, those nanoparticles having p-isononylphenoxypoly(glycidol) as a surfactant also have albumin associated therewith to increase stability.

This invention further discloses a method of making nanoparticles having p-isononylphenoxypoly(glycidol) as a surface modifier adsorbed on the surface thereof, said method comprising contacting said nanoparticles with the surfactant for a time and under conditions sufficient to form a surface modified nanoparticle. In a preferred embodiment, the method further comprises contacting the surface modified nanoparticle with albumin for a time and under conditions sufficient to form a stabilized surface modified nanoparticle.

DETAILED DESCRIPTION OF THE INVENTION

Figure 1:
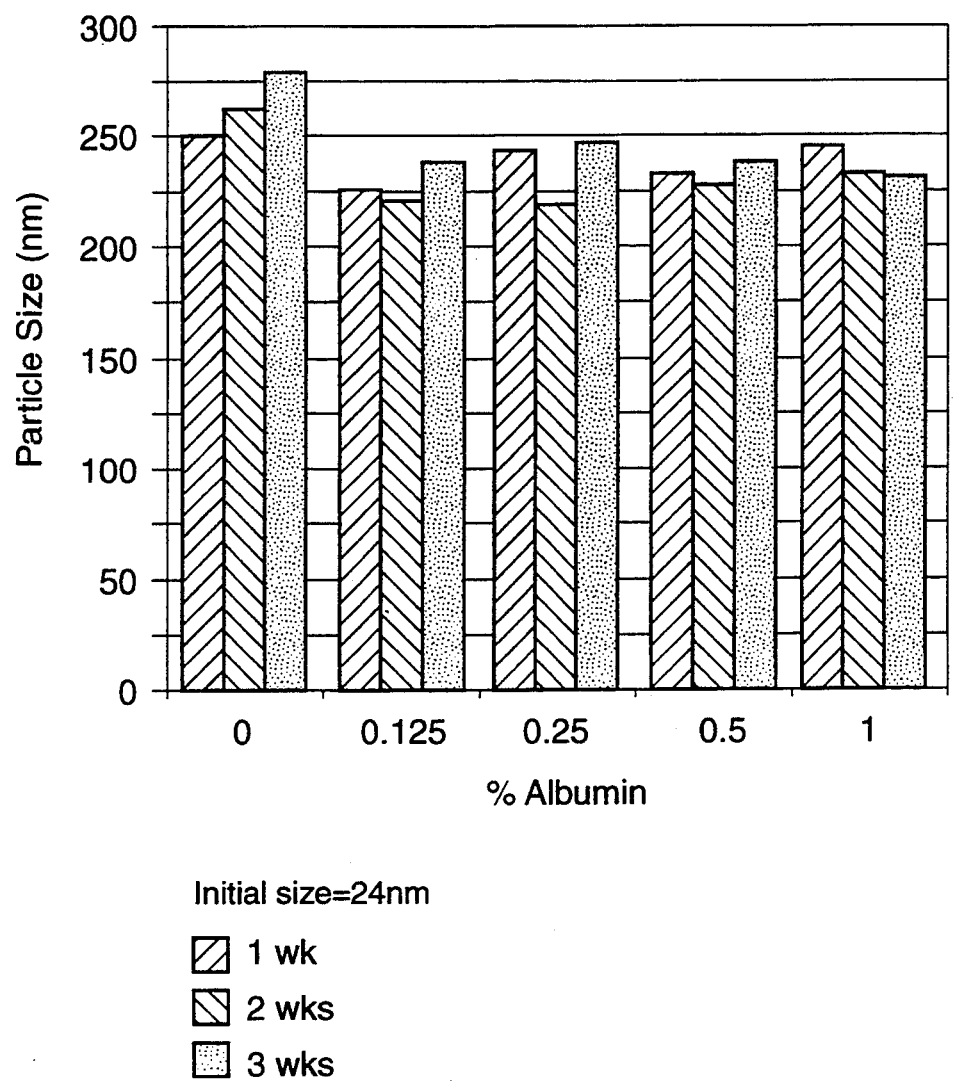
FIGS. 1-4 are bar graphs showing particle size growth as a function of albumin concentration under various storage conditions for two preferred embodiments of the invention.

This invention is described hereinafter primarily in connection with nanoparticles having p-isononylphenoxypoly(glycidol) as a surface modifier. In addition, the invention is believed to be useful in conjunction with other polyglycidol surface modifiers.

This invention is directed to a composition comprised of nanoparticles having p-isononylphenoxypoly(glycidol) as a surface modifier adsorbed on the surface thereof. In a preferred embodiment, p-isononylphenoxypoly(glycidol) is present in an amount sufficient to allow autoclaving of the nanoparticles while preventing agglomeration.

The nanoparticles useful in the practice of this invention include a surface modifier. Surface modifiers useful herein physically adhere to the surface of the diagnostic or therapeutic agent therein, but do not chemically react with the agent or itself. A surface modifier useful in the present invention is p-isononylphenoxypoly(glycidol). P-isononylphenoxypoly(glycidol), also known as Olin-10G or Surfactant 10-G, is commercially available as 10G$^R$ from Olin Chemicals, Stamford, Connecticut, and is hereinafter referred to as "Olin-10G".

This surface modifier is commercially available and/or can be prepared by techniques known in the art.

The nanoparticles useful in the practice of this invention can be prepared according to the methods disclosed in U.S. Pat. No. 5,145,684, whose disclosure is incorporated herein by reference. Briefly, nanoparticles are prepared by dispersing a poorly soluble therapeutic or diagnostic agent in a liquid dispersion medium and wet-grinding the agent in the presence of grinding media to reduce the particle size of the contrast agent to an effective average particle size of less than about 400 nm. The particles can be reduced in size in the presence of a surface modifier.

A general procedure for preparing the particles useful in the practice of this invention follows. The therapeutic or diagnostic agent selected is obtained commercially and/or prepared by techniques known in the art as described above, in a conventional coarse form. It is preferred, but not essential, that the particle size of the coarse therapeutic or diagnostic substance selected be less than about 100 $\mu$m as determined by sieve analysis. If the coarse particle size of that agent is greater than about 100 $\mu$m, then it is preferred that the coarse particles of the therapeutic or diagnostic agent be reduced in size to less than 100 $\mu$m using a conventional milling method such as airjet or fragmentation milling.

The coarse therapeutic or diagnostic agent selected can then be added to a liquid medium in which it is essentially insoluble to form a premix. The concentration of the therapeutic or diagnostic agent in the liquid medium can vary from about 0.1–60%, and preferably is from 5–30% (w/w). It is preferred, but not essential, that the surface modifier be present in the premix. The concentration of the surface modifier can vary from about 0.1 to 90%, and preferably is 1–75%, more preferably 2–50% and most preferably 5–45% by weight based on the total combined weight of the drug substance and surface modifier. The apparent viscosity of the premix suspension is preferably less than about 1000 centipoise.

The premix can be used directly by wet grinding to reduce the average particle size in the dispersion to less than 400 nm. It is preferred that the premix be used directly when a ball mill is used for attrition. Alternatively, the therapeutic or diagnostic agent and, optionally, the surface modifier, can be dispersed in the liquid medium using suitable agitation, e.g., a roller mill or a Cowles type mixer, until a homogeneous dispersion is observed in which there are no large agglomerates visible to the naked eye. It is preferred that the premix be subjected to such a premilling dispersion step when a recirculating media mill is used for attrition.

Wet grinding can take place in any suitable dispersion mill, including, for example, a ball mill, an attritor mill, a vibratory mill, a planetary mill and media mills such as a sand mill and a bead mill. A media mill is preferred due to the relatively shorter milling time required to provide the intended result, i.e., the desired reduction in particle size. For media milling, the apparent viscosity of the premix preferably is from about 100 to about 1000 centipoise. For ball milling, the apparent viscosity of the premix preferably is from about 1 up to about 100 centipoise. Such ranges tend to afford an optimal balance between efficient particle fragmentation and media erosion.

The grinding media for the particle size reduction step can be selected from rigid media preferably spherical or particulate in form having an average size less than about 3 mm and, more preferably, less than about 1 mm. Such media desirably can provide the particles of the invention with shorter processing times and impart less wear to the milling equipment. The selection of material for the grinding media is not believed to be critical. However, media with higher density, e.g., glass (2.6 g/cm$^3$), zirconium silicate (3.7 g/cm$^3$), and zirconium oxide (5.4 g/cm$^3$), are generally preferred for more efficient milling. Zirconium oxide, such as 95% ZrO stabilized with magnesia, zirconium silicate, and glass grinding media provide particles having levels of contamination which are believed to be acceptable for the preparation of therapeutic or diagnostic compositions. However, other media, such as stainless steel, titania, alumina, and 95% ZrO stabilized with yttrium, are believed to be useful. In addition, polymeric media having a density typically from 1 to 2 g/cm$^3$ are also expected to be useful under certain milling conditions.

The attrition time can vary widely and depends primarily upon the particular wet grinding mill selected. For ball mills, processing times of up to five days or longer may be required. On the other hand, processing times of less than 1 day (residence times of about one minute up to several hours) have provided the desired results using a high shear media mill.

The particles must be reduced in size at a temperature which does not significantly degrade the therapeutic or diagnostic agent. Processing temperatures of less than about 30°–40° C. are ordinarily preferred. If desired, the processing equipment can be cooled with conventional cooling equipment. The method is conveniently carried out under conditions of ambient temperature and at processing pressures which are safe and effective for the milling process. For example, ambient processing pressures are typical of ball mills, attritor mills and vibratory mills. Processing pressures up to about 20 psi (1.4 kg/cm$^2$) are typical of media milling.

The surface modifier, if not present in the premix, must be added to the dispersion after attrition in an amount as described for the premix. Thereafter, the dispersion can be mixed, e.g., by shaking vigorously. Optionally, the dispersion can be subjected to a sonication step, e.g., using an ultrasonic power supply. For example, the dispersion can be subjected to ultrasonic energy having a frequency of 20–80 kHz for a time of about 1 to 120 seconds.

The relative amount of therapeutic or diagnostic agent and surface modifier can vary widely and the optimal amount of the surface modifier can depend, for example, upon the particular therapeutic or diagnostic agent and surface modifier selected, the critical micelle concentration of the surface modifier if it forms micelles, the hydrophilic lipophilic balance (HLB) of the stabilizer, the melting point of the stabilizer, its water solubility, the surface tension of water solutions of the stabilizer, etc. The surface modifier preferably is present in an amount of about 0.1–10 mg per square meter surface area of the therapeutic or diagnostic agent. The surface modifier can be present in an amount of 0.1–90%, preferably 1–75%, more preferably 2–50%, and most preferably 5–45% by weight based on the total weight of the dry particle.

Therapeutic and diagnostic agents useful in the composition of the present invention include those disclosed in U.S. Pat. No. 5,145,684, and EP-A 498,482 whose disclosures are incorporated herein by reference. Preferred diagnostic agents include the x-ray imaging agent WIN-8883 (ethyl 3,5-diacetamido-2,4,6-triiodobenzoate) also known as the ethyl ester of diatrazoic acid (EEDA), WIN 67722, i.e., (6-ethoxy-6-oxohexyl-3,5-bis(acetamido)-2,4,6-triiodobenzoate; ethyl-2-(3,5-bis-(acetamido)-2,4,6-triiodobenzoyloxy) butyrate (WIN 16318); ethyl diatrizoxyacetate (WIN 12901); ethyl 2-(3,5-bis (acetamido) -2,4,6-triiodobenzoyloxy)propionate (WIN 16923); N-ethyl 2-(3,5-bis (acetamido)-2,4,6-triiodobenzoyloxy acetamide (WIN 65312); isopropyl 2-(3,5-bis (acetamido) -2,4,6-triiodobenzoyloxy) acetamide (WIN 12855); diethyl 2-(3,5-bis(acetamido)-2,4,6-triiodobenzoyloxy malonate (WIN 67721); and ethyl 2-(3,5-bis (acetamido) -2,4,6-triiodobenzoyloxy) phenylacetate (WIN 67585).

As used herein, particle size refers to a number average particle size as measured by conventional particle size measuring techniques well known to those skilled in the art, such as sedimentation field flow fractionation, photon correlation spectroscopy, or disk centrifugation. The phrase "an effective average particle size of less than about 400 nm" as used herein means that at least 90% of the particles have a number average particle size of less than about 400 nm when measured by the above-noted techniques. In preferred embodiments of the invention, the effective average particle size is less than about 300 nm, and more preferably less than about 250 nm. In some embodiments of the invention, an effective average particle size of less than about 200 nm has been achieved. With reference to the effective average particle size, it is preferred that at least 95% and, more preferably, at least 99% of the particles have a particle size less than the effective average, e.g., 400 nm. In particularly preferred embodiments, essentially all of the particles have a size less than 400 nm. In some embodiments, essentially all of the particles have a size less than 250 nm.

A method for the preparation of a nanoparticle composition according to this invention includes the steps of introducing a therapeutic or diagnostic agent, a liquid medium, grinding media, and optionally, a surface modifier into a grinding vessel; wet grinding to reduce the particle size of the therapeutic or diagnostic agent to less than about 400 nm; and separating the particles and the liquid medium from the grinding vessel and grinding media, for example, by suction, filtration or evaporation. If the surface modifier is not present during wet grinding, it can be admixed with the particles thereafter. The liquid medium, most often water, can serve as the pharmaceutically acceptable carrier. The method can be carried out under aseptic conditions. Thereafter, the nanoparticle composition preferably is subjected to a sterilization process.

As noted elsewhere herein, sterile filtration will not provide adequate sterilization for nanoparticles without causing significant loss of active material. Therefore, other methods of sterilization are required. For example, steam or moist heat sterilization at temperatures of about 121° C. for a time period of about 20 minutes can be used. At altitudes near sea level, such conditions are attained by using steam at a pressure of 15 pounds per square inch (psi) in excess of atmospheric pressure.

Dry heat sterilization may also be performed, although the temperatures used for dry heat sterilization are typically 160° C. for time periods of 1 to 2 hours.

Sterilization takes place in the presence of the surfactant p-isononylphenoxypoly(glycidol), which minimizes particle size growth during sterilization. This surfactant is stable at least to temperatures of 160° C.

Stability refers to the ability of the nanoparticle composition to remain substantially unchanged upon storage under appropriate temperature and humidity conditions. One measure of the stability of a nanoparticle composition is the ability of that composition not to agglomerate or Ostwald ripen over time. Hence, by measuring increases in particle size over time, the stability of a particular nanoparticle composition can be determined.

A stability enhancing (increasing) compound is one which increases the stability of a nanoparticle suspension, as evidenced by a decrease in the amount of particle size increase in the presence of the stability enhancing compound, relative to the amount of particle size increase in the absence of the stability enhancing compound.

In a preferred embodiment, the stability of a nanoparticle composition with p-isononylphenoxypoly(glycidol) as a surface modifier is increased by the addition of albumin, as a stability enhancing compound, to the nanoparticle composition such that the albumin is associated therewith. Blood serum albumin is the major blood serum protein in mammals, found at a concentration of about 40 grams per liter in humans. In addition to blood serum albumin, other sources of albumin include ovalbumin from eggs, and whey albumin from milk. Other animal sources of albumin include cattle, baboons, cat, chicken, dog, donkey, goat, guinea pig, hamster, horse, mouse, pig, pigeon, rabbit, rat, rhesus monkey, sheep, and turkey. A preferred albumin is blood serum albumin. A preferred blood serum albumin is bovine serum albumin.

The amount of albumin present in the compositions of the present invention depends upon many factors, including the therapeutic or diagnostic agent used in the nanoparticles, the concentration of Olin-10G present, the particular storage conditions of the nanoparticles, the time of storage, the particular use envisioned for the nanoparticles, and the like. A preferred amount of albumin in the compositions of the present invention is from about 10 to about 0.01% of the total weight of the nanoparticle. A more preferred amount is from about 5 to about 0.1% of the total weight of the nanoparticle. In preferred embodiments, the relative amounts by weight of the albumin and Olin-10G present range from about 1:25 to 25:1.

This invention further discloses a method of making nanoparticles having p-isononylphenoxypoly(glycidol) as a surface modifier adsorbed on the surface thereof, comprised of contacting said nanoparticles with p-isononylphenoxypoly(glycidol) for a time and under conditions sufficient to form a p-isononylphenoxypoly(glycidol) stabilized nanoparticle.

This method involves the preparation of therapeutic or diagnostic nanoparticles, as discussed elsewhere herein, and contacting those nanoparticles with p-isononylphenoxypoly(glycidol). Contacting may be by admixing a suspension of nanoparticles with a solution of p-isononylphenoxypoly(glycidol).

In a preferred embodiment, the contacting is followed by heat treatment at a given temperature and for a time sufficient to effect sterilization of the nanoparticle suspension.

In a further preferred embodiment, this method involves the further step of contacting the p-isononylphenoxypoly(glycidol) stabilized nanoparticles with a stability enhancing compound for a time and under conditions sufficient to form p-isononylphenoxypoly(glycidol) stabilized nanoparticles with albumin associated therewith.

Contacting may be by admixing a solution of the stability enhancing compound with a nanoparticle suspension of a diagnostic or therapeutic agent previously stabilized with p-isononylphenoxypoly(glycidol). A preferred stability enhancing compound is albumin. A preferred albumin is blood serum albumin. A preferred blood serum albumin is bovine serum albumin.

The following examples further illustrate the invention and are not to be construed as limiting of the specification and claims in any way.

EXAMPLE 1

The Effects of Olin-10G on Heat Stability

Nanoparticle suspensions containing various diagnostic agents were made according to the methods discussed elsewhere herein, using various concentrations of Olin-10G as a surface active agent. These nanoparticles were then tested for their stability in the presence or absence of heating, and in the presence of phosphate buffered saline, pH 7.4 (PBS), or rat plasma. The results are shown in the following tables.

TABLE 1

| | 15% Compound/4% Olin 10G | | | | |
|---|---|---|---|---|---|
| WIN Compound | Size (nm) Before Autoclave | Size (nm) After Autoclave 110° C. 1 hr | Size (nm) After Autoclave 121° C. 20 min | Fluid Stability PBS (pH = 7.4) | Fluid Stability Rat Plasma |
| 8883 | 242 | 337 | 355 | stable | unstable |
| 16923 | 262 | 336 | 351 | stable | unstable |
| 65312 | 175 | 294 | 284 | unstable | stable |
| 12901 | 323 | 444 | 383 | stable | unstable |
| 12855 | 289 | 436 | 368 | unstable | unstable |
| 67721 | 189 | 322 | 300 | stable | stable |
| 67722 | 242 | 274 | 281 | stable | stable |

Olin-10G stabilized seven of nine cores evaluated to a particle size below 400 nm. All seven samples autoclaved at 121° C. for 20 minutes retained a mean particle size below 400 nm. This demonstrates that Olin-10G provides good resistance to significant particle size growth during autoclaving.

TABLE 2

| | | 15% WIN 67722 | | | | |
|---|---|---|---|---|---|---|
| % Olin-10G | Particle Size (nm) | Size (nm) 3 Week Physical Stability | After Autoclave 110° C.-1 hr size (nm) | After Autoclave 121° C.-20 min size (nm) | After Autolcave Fluid Stability PBS (pH = 7.4) | After Autolcave Fluid Stability Rat Plasma |
| 4 | 165 | 268 | 289 | 331 | unstable | stable |
| 3 | 171 | 270 | 297 | 326 | unstable | stable |
| 2 | 176 | 270 | 313 | 382 | unstable | stable |
| 1 | 268 | 312 | 432 | not done | unstable | stable |

TABLE 3

| | | 15% WIN 67585 | | | | |
|---|---|---|---|---|---|---|
| % Olin-10G | Particle Size (nm) | Size (nm) 3 Week Physical Stability | After Autoclave 110° C.-1 hr size (nm) | After Autoclave 121° C.-20 min size (nm) | After Autolcave Fluid Stability PBS (pH = 7.4) | After Autolcave Fluid Stability Rat Plasma |
| 4 | 169 | 213 | 339 | not done | stable | stable |
| 3 | 170 | 216 | 368 | not done | stable | stable |
| 2 | 170 | 229 | 367 | not done | stable | stable |
| 1 | >2000 | >2000 | 614 | not done | unstable | unstable |

For both WIN 67722 and WIN 67585, particle size growth was observed when stored at room temperature for about 2–3 weeks. However, these nanoparticles, upon further heat treatment at either 110° C./1 hr or 121° C./20 rain resulted in relatively small increase in particle size as long as Olin-10G concentration was >1% w/v. This Olin 10G concentration effect was more pronounced with WIN 67585 compared to WIN 67722.

EXAMPLE 2

The Effects of Olin-10G and BSA on Heat and Shelf Stability

Nanoparticle suspensions containing various diagnostic agents were made according to the methods discussed elsewhere herein, using various concentrations of Olin-10G as a surface active agent and bovine serum albumin (BSA) as a stability enhancing compound. These nanoparticles were then tested for their stability in the presence or absence of heating, and in the presence of phosphate buffered saline (PBS) or rat plasma. The results are shown in the following tables.

In the first experiment, a 15% WIN 67722 suspension stabilized with 2% Olin-10G (mean particle size 271 nm) was diluted with Bovine Serum Albumin (Sigma, 96-99%) to give final (w/v) concentrations of 11.25/1.5/0.5% (WIN 67722/Olin-10G/Albumin). No growth in particle size was detected after 1 week storage, after autoclaving at 110° C. for 60 minutes or 21° C. for 20 minutes, and for 2 weeks storage post-autoclaving. In addition, these nanoparticles were stable in both pH 7.4 PBS buffer and rat plasma.

Thereafter, studies were conducted at various albumin concentrations on both WIN 8883 and WIN 67722 nanoparticles having Olin-10G adsorbed thereon at the following concentrations (which represent approximately equivalent iodine content).

| | Concentration (% w/v) | [Olin-10G1] (% w/v) |
|---|---|---|
| WIN 8883 | 15 | 3 |
| WIN 67722 | 17.7 | 4.72 |

Figure 2:
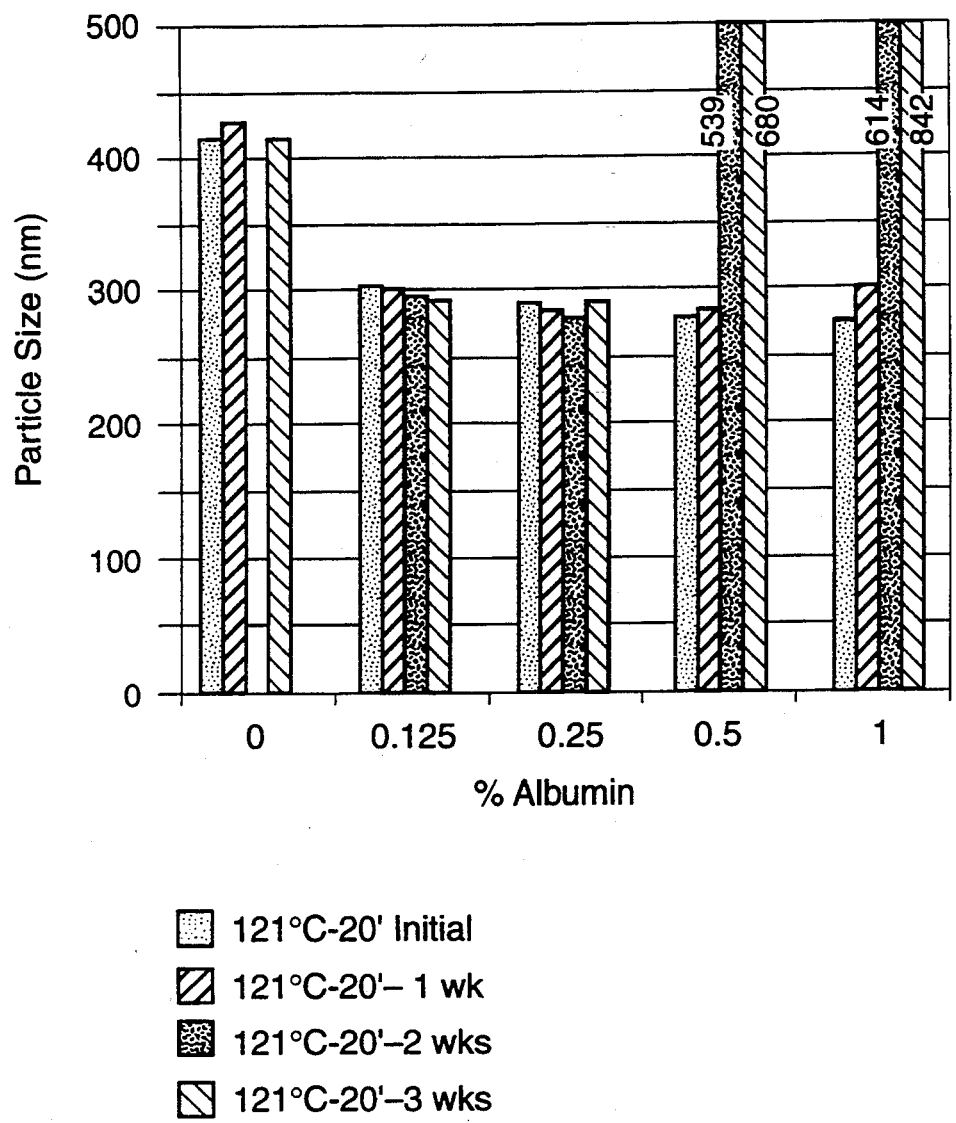

In the case of WIN 8883-Olin-10G, FIGS. 1 and 2 indicate that the addition of albumin at all concentrations increased shelf stability. The preferred albumin concentrations for heat stress and subsequent room temperature (shelf) stability were 0.125 and 0.25 percent.

Figure 3:
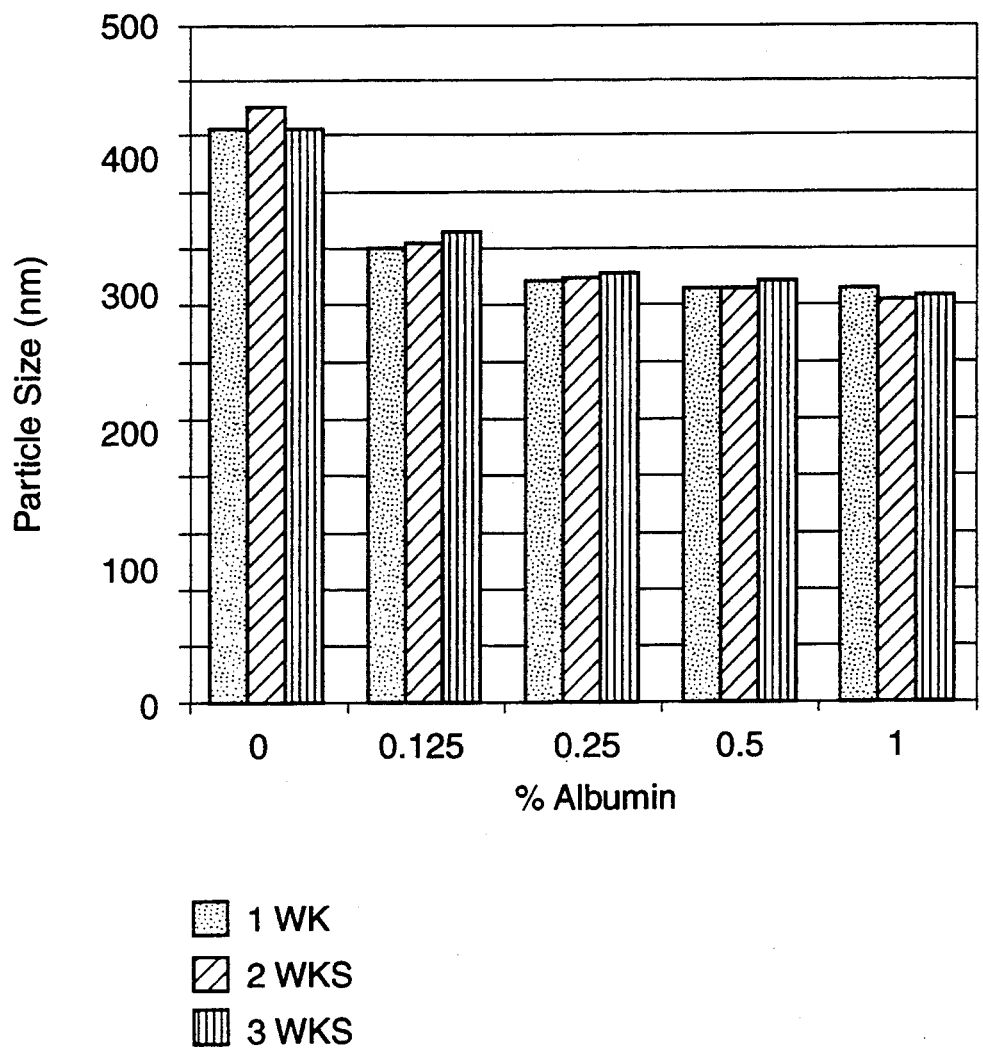
Figure 4:
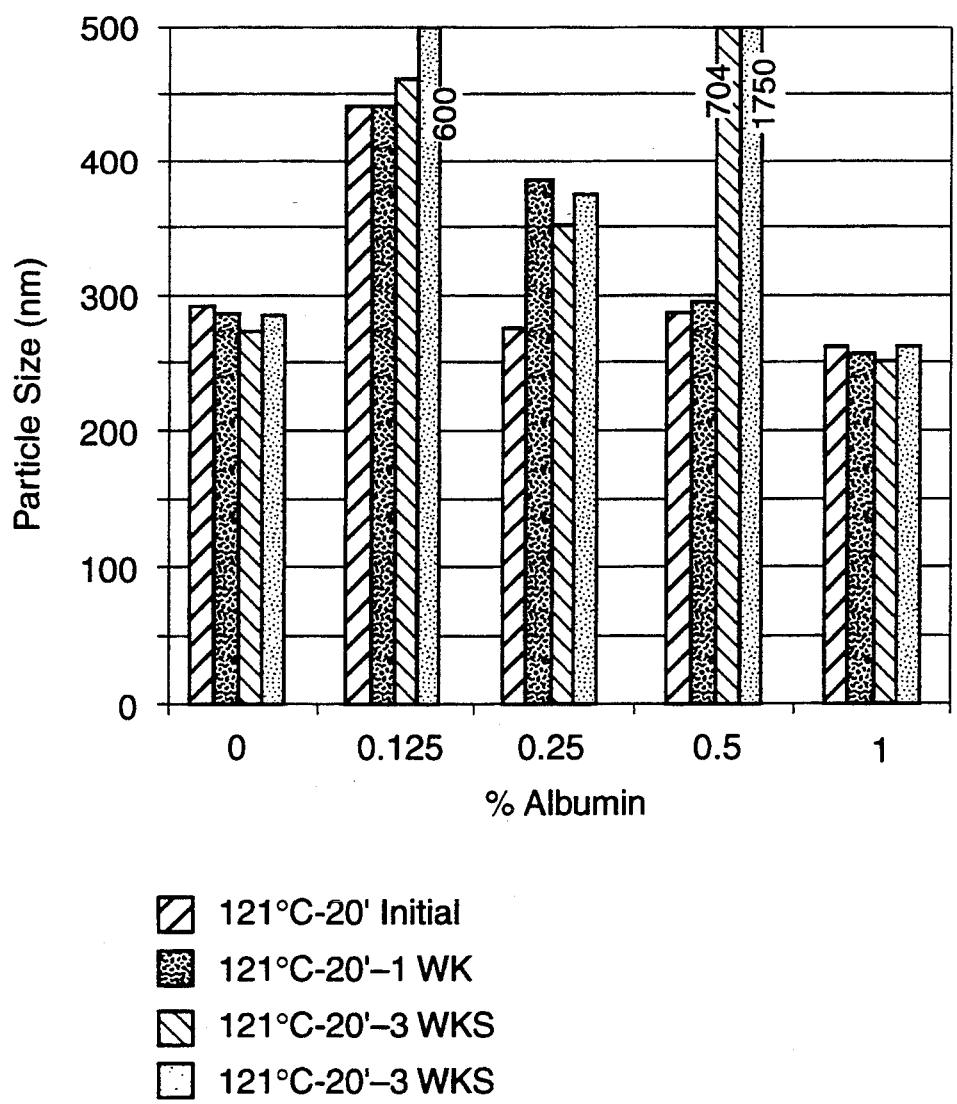

In the case of WIN 67722-Olin-10G, FIGS. 3 and 4 indicate that the addition of albumin at all concentrations increased shelf stability. The preferred albumin concentrations for heat stress and subsequent room temperature stability were greater than 0.5 percent.

The foregoing specification, including the specific embodiments and examples is intended to be illustrative of the present invention and is not to be taken as limiting. Numerous other variations and modifications can be effected without departing from the true spirit and scope of the present invention.

We claim:

1. A heat sterilized composition comprised of nanoparticles consisting essentially of a diagnostic or therapeutic agent having at least one surface modifier adsorbed on the surface thereof and having p-isononylphenoxypoly(glycidol) in an amount of 1–75% by weight based on the total weight of said nanoparticles as said surface modifier, wherein said nanoparticles are resistant to particle size growth when said composition is heat sterilized at 121° C. for 20 minutes.

2. The composition of claim 1 wherein said diagnostic agent is ethyl 3,5-diacetamido-2,4,6-triiodobenzoate.

3. The composition of claim 1 wherein said diagnostic agent is 6-ethoxy-6-oxohexyl-3,5-bis(acetylamino)-2,4,6-triiodobenzoate.

4. The composition of claim 1 further comprising a stability enhancing compound.

5. The composition of claim 4 wherein said stability enhancing compound is albumin.

6. The composition of claim 5 wherein said albumin is a blood serum albumin.

7. The composition of claim 5 wherein said blood serum albumin is bovine serum albumin.

8. The composition of claim 1 in wherein said p-isononylphenoxypoly(glycidol) is present in an amount sufficient for the sterilization of the nanoparticles.

* * * * *